(12) United States Patent
Mollison et al.

(10) Patent No.: US 7,960,405 B2
(45) Date of Patent: Jun. 14, 2011

(54) COMPOUNDS AND METHODS FOR TREATMENT AND PREVENTION OF DISEASES

(75) Inventors: Karl W. Mollison, Arlington, IL (US); Angela M. LeCaptain, Silver Lake, WI (US); Sandra E. Burke, Libertyville, IL (US); Keith R. Cromack, Gurnee, IL (US); Peter J. Tarcha, Lake Villa, IL (US); Yen-Chih J. Chen, Evanston, IL (US); John L. Toner, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 1224 days.

(21) Appl. No.: 11/565,507

(22) Filed: Nov. 30, 2006

(65) Prior Publication Data

US 2008/0171763 A1 Jul. 17, 2008

Related U.S. Application Data

(60) Continuation-in-part of application No. 10/235,572, filed on Sep. 6, 2002, now abandoned, which is a continuation of application No. 09/950,307, filed on Sep. 10, 2001, now Pat. No. 6,890,546, which is a continuation-in-part of application No. 09/433,001, filed on Nov. 2, 1999, now Pat. No. 6,329,386, which is a division of application No. 09/159,945, filed on Sep. 24, 1998, now Pat. No. 6,015,815.

(51) Int. Cl.
*C07D 498/18* (2006.01)
*A61K 31/445* (2006.01)
*A61P 41/00* (2006.01)

(52) U.S. Cl. ........................ 514/291; 540/456
(58) Field of Classification Search .................. 540/456; 514/291
See application file for complete search history.

(56) References Cited

U.S. PATENT DOCUMENTS

| | | | |
|---|---|---|---|
| 4,580,568 A | 4/1986 | Gianturco | |
| 4,733,665 A | 3/1988 | Palmaz | |
| 4,916,193 A | 4/1990 | Tang et al. | |
| 4,994,071 A | 2/1991 | MacGregor | |
| 5,092,877 A | 3/1992 | Pinchuk | |
| 5,163,952 A | 11/1992 | Froix | |
| 5,260,300 A | 11/1993 | Hu | |
| 5,304,121 A | 4/1994 | Sahatjian | |
| 5,346,893 A | 9/1994 | Failli et al. | |
| 5,355,832 A | 10/1994 | Loh et al. | |
| 5,380,299 A | 1/1995 | Fearnot et al. | |
| 5,447,724 A | 9/1995 | Helmus et al. | |
| 5,447,799 A | 9/1995 | Loh et al. | |
| 5,464,650 A | 11/1995 | Berg et al. | |
| 5,527,907 A | 6/1996 | Or et al. | |
| 5,583,139 A | 12/1996 | Or et al. | |
| 5,605,696 A | 2/1997 | Eury et al. | |
| 5,624,411 A | 4/1997 | Tuch | |
| 5,672,605 A | 9/1997 | Or et al. | |
| 5,705,583 A | 1/1998 | Bowers et al. | |
| 5,755,771 A | 5/1998 | Penn et al. | |
| 5,824,049 A | 10/1998 | Ragheb et al. | |
| 5,873,904 A | 2/1999 | Ragheb et al. | |
| 6,015,815 A | 1/2000 | Mollison | |
| 6,033,434 A | 3/2000 | Borghi | |
| 6,083,257 A | 7/2000 | Taylor et al. | |
| 6,090,901 A | 7/2000 | Bowers et al. | |
| 6,106,548 A | 8/2000 | Roubin et al. | |
| 6,248,129 B1 | 6/2001 | Froix | |
| 6,273,913 B1 | 8/2001 | Wright et al. | |
| 6,284,305 B1 | 9/2001 | Ding et al. | |
| 6,299,604 B1 | 10/2001 | Ragheb et al. | |
| 6,329,386 B1 | 12/2001 | Mollison | |
| 6,358,556 B1 | 3/2002 | Ding et al. | |
| 6,419,692 B1 | 7/2002 | Yang et al. | |
| 6,585,764 B2 | 7/2003 | Wright et al. | |
| 2001/0029351 A1 | 10/2001 | Falotico et al. | |
| 2002/0123505 A1 | 9/2002 | Mollison et al. | |
| 2002/0127263 A1 | 9/2002 | Carlyle et al. | |

FOREIGN PATENT DOCUMENTS

| | | |
|---|---|---|
| EP | 1 236 478 | 2/2002 |
| WO | WO 94/15583 | 7/1994 |
| WO | WO 99/15530 | 4/1999 |
| WO | WO 01/87372 | 11/2001 |
| WO | WO 02/26281 | 4/2002 |
| WO | WO 02/055122 | 7/2002 |
| WO | WO 02/066092 | 8/2002 |

OTHER PUBLICATIONS

Alt et al., "Inhibition of Neointima Formation After Experimental Coronary Artery Stenting; A New Biodegradable Stent Coating Releasing Hirudin and the Prostacyclin Analogue Iloprost", Circulation, pp. 1453-1458 (2000).
Burke et al., "Neointimal Formation After Ballon-Induced Vascular Injury in Yucatan Minipigs is Reduced by Oral Rapamycin", Journal for Cardiovascular Pharmacology vol. 33, pp. 829-835 (1999).
Gallo, MD, et al., "Inhibition of Intimal Thickening After Ballon Angioplasty in Porcine Coronary Arteries by Targeting Regulators of the Cell Cycle", Circulation, pp. 2164-2170 (1999).
Michael Poon et al., "Rapamycin Inhibits Vascular Smooth Muscle Cell Migration", Journal of Clinical Investigation, vol. 98, No. 10, pp. 2277-2283 (1996).
Sousa et al., "Lack of Neointimal Proliferation After Implantation of Sirolimus-Coated Stents in Human Coronary Arteries", Circulation, pp. 192-194 (2001).

*Primary Examiner* — Bruck Kifle
(74) *Attorney, Agent, or Firm* — Squire Sanders & Dempsey, (US) LLP

(57) ABSTRACT

A prodrug compound of a rapamycin analog and methods for inhibiting, treating, and preventing mammalian diseases.

6 Claims, 2 Drawing Sheets

The Bio*div Y sio* PC-coated Stent
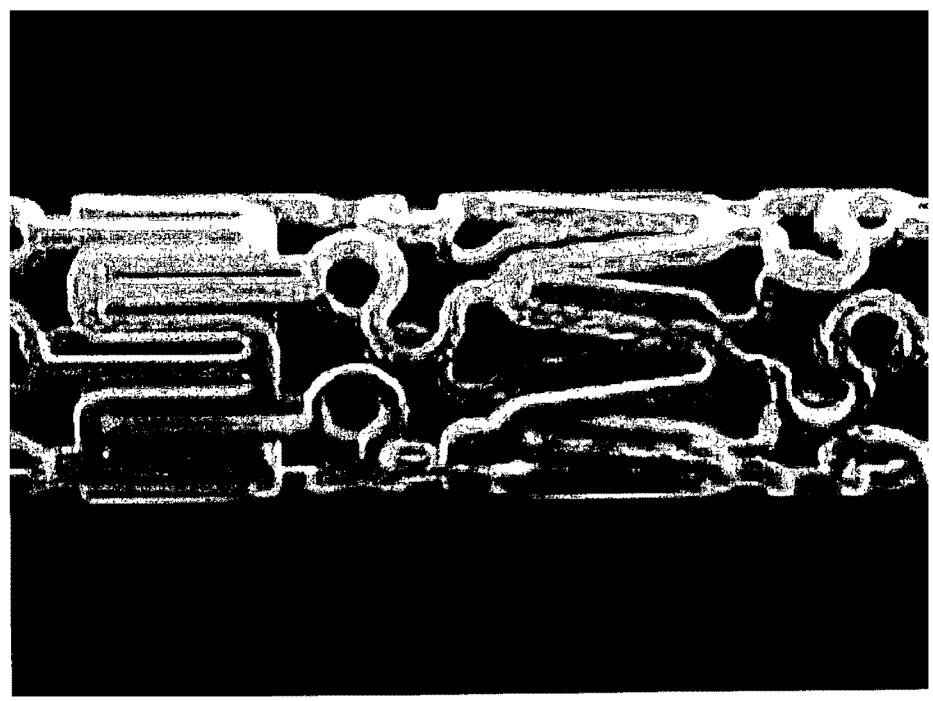
FIG. 2
Polymer Only
Polymer Plus Drug
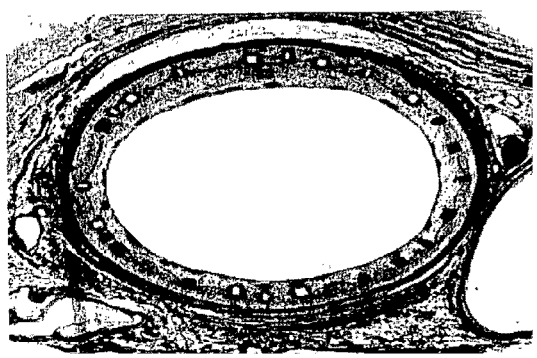
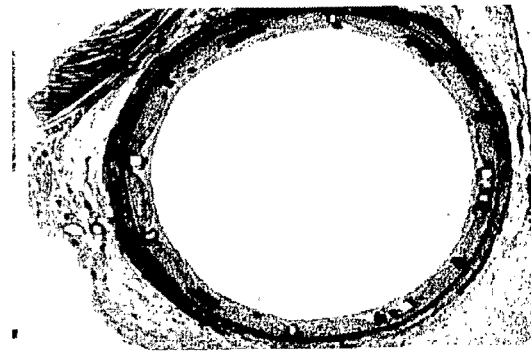
FIG. 3A
FIG. 3B

COMPOUNDS AND METHODS FOR TREATMENT AND PREVENTION OF DISEASES

CROSS-REFERENCE TO RELATED APPLICATIONS

This application is a continuation-in-part of U.S. Ser. No. 10/235,572, filed on Sep. 6, 2002, which is a continuation of U.S. Ser. No. 09/950,307, filed Sep. 10, 2001, which is a continuation-in-part of U.S. Ser. No. 09/433,001, filed Nov. 2, 1999, which is a divisional of U.S. Ser. No. 09/159,945, filed Sep. 24, 1998, now U.S. Pat. No. 6,015,815, incorporated herein by reference.

BACKGROUND OF THE INVENTION

1. The Field of the Invention

The invention relates to compounds and methods for treating and preventing of restenosis. More particularly, the invention relates to prodrugs of rapamycin and methods of treatment employing the same.

2. The Relevant Technology

The compound cyclosporine (cyclosporin A) has found wide use since its introduction in the fields of organ transplantation and immunomodulation, and has brought about a significant increase in the success rate for transplantation procedures. Recently, several classes of macrocyclic compounds having potent immunomodulatory activity have been dis propiopyl covered. Okuhara et al., in European Patent Application No. 184,162, published Jun. 11, 1986, disclose a number of macrocyclic compounds isolated from the genus *Streptomyces*, including the immunosuppressant FK-506, a 23-membered macrocyclic lactone, which was isolated from a strain of *S. tsukubaensis*.

Other related natural products, such as FR-900520 and FR-900523, which differ from FK-506 in their alkyl substituent at C-21, have been isolated from *S. hygroscopicus yakushimnaensis*. Another analog, FR-900525, produced by *S. tsukubaensis*, differs from FK-506 in the replacement of a pipecolic acid moiety with a proline group. Unsatisfactory side-effects associated with cyclosporine and FK-506 such as nephrotoxicity, have led to a continued search for immunosuppressant compounds having improved efficacy and safety, including an immunosuppressive agent which is effective topically, but ineffective systemically (U.S. Pat. No. 5,457,111).

Rapamycin is a macrocyclic triene antibiotic produced by *Streptomyces hygroscopicus*, which was found to have antifungal activity, particularly against *Candida albicans*, both in vitro and in vivo (C. Vezina et al., *J. Antibiot.* 1975, 28, 721; S. N. Sehgal et al., *J. Antibiot.* 1975, 28, 727; H. A. Baker et al., *J. Antibiot.* 1978, 31, 539; U.S. Pat. No. 3,929,992; and U.S. Pat. No. 3,993,749).

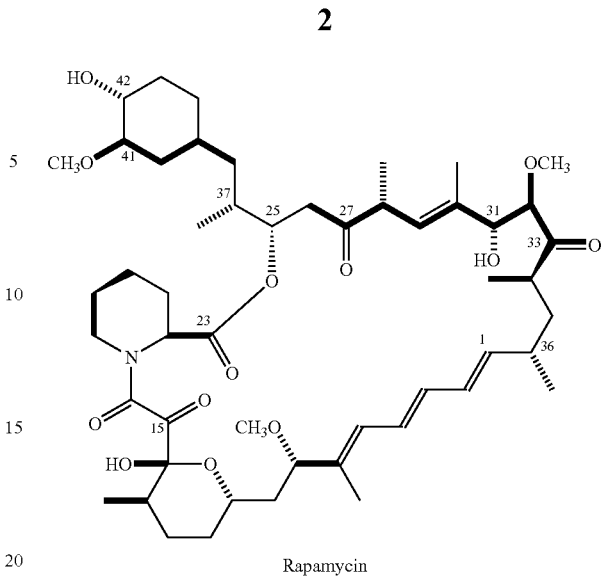

Rapamycin

Rapamycin alone (U.S. Pat. No. 4,885,171) or in combination with picibanil (U.S. Pat. No. 4,401,653) has been shown to have antitumor activity. In 1977, rapamycin was also shown to be effective as an immunosuppressant in the experimental allergic encephalomyelitis model, a model for multiple sclerosis; in the adjuvant arthritis model, a model for rheumatoid arthritis; and was shown to effectively inhibit the formation of IgE-like antibodies (R. Martel et al., *Can. J. Physiol. Pharmacol.*, 1977, 55, 48).

The immunosuppressive effects of rapamycin have also been disclosed in *FASEB*, 1989, 3, 3411 as has its ability to prolong survival time of organ grafts in histoincompatible rodents (R. Morris, *Med. Sci. Res.*, 1989, 17, 877). The ability of rapamycin to inhibit T-cell activation was disclosed by M. Strauch (*FASEB*, 1989, 3, 3411). These and other biological effects of rapamycin are reviewed in *Transplantation Reviews*, 1992, 6, 39-87.

Rapamycin has been shown to reduce neointimal proliferation in animal models, and to reduce the rate of restenosis in humans. Evidence has been published showing that rapamycin also exhibits an anti-inflammatory effect, a characteristic which supported its selection as an agent for the treatment of rheumatoid arthritis. Because both cell proliferation and inflammation are thought to be causative factors in the formation of restenotic lesions after balloon angioplasty and stent placement, rapamycin and analogs thereof have been proposed for the prevention of restenosis.

Mono-ester and di-ester derivatives of rapamycin (esterification at positions 31 and 42) have been shown to be useful as antifungal agents (U.S. Pat. No. 4,316,885) and as water soluble prodrugs of rapamycin (U.S. Pat. No. 4,650,803).

Fermentation and purification of rapamycin and 30-demethoxy rapamycin have been described in the literature (C. Vezina et al. *J. Antibiot.* (Tokyo), 1975, 28 (10), 721; S. N. Sehgal et al., *J. Antibiot.* (Tokyo), 1975, 28(10), 727; 1983, 36(4), 351; N. L. Pavia et al., *J. Natural Products*, 1991, 54(1), 167-177).

Numerous chemical modifications of rapamycin have been attempted. These include the preparation of mono- and di-ester derivatives of rapamycin (WO 92/05179), 27-oximes of rapamycin (EPO 467606); 42-oxo analog of rapamycin (U.S. Pat. No. 5,023,262); bicyclic rapamycins (U.S. Pat. No. 5,120,725); rapamycin dimers (U.S. Pat. No. 5,120,727); silyl ethers of rapamycin (U.S. Pat. No. 5,120,842); and arylsulfonates and sulfamates (U.S. Pat. No. 5,177,203). Rapamycin was recently synthesized in its naturally occurring enantiomeric form (K. C. Nicolaou et al., *J. Am. Chem. Soc.*, 1993, 115, 4419-4420; S. L. Schreiber, *J. Am. Chem. Soc.*, 1993, 115, 7906-7907; S. J. Danishefsky, *J. Am. Chem. Soc.*, 1993, 115, 9345-9346.

It has been known that rapamycin, like FK-506, binds to FKBP-12 (Siekierka, J. J.; Hung, S. H. Y.; Poe, M.; Lin, C. S.; Sigal, N. H. *Nature,* 1989, 341, 755-757; Harding, M. W.; Galat, A.; Uehling, D. E.; Schreiber, S. L. *Nature* 1989, 341, 758-760; Dumont, F. J.; Melino, M. R.; Staruch, M. J.; Koprak, S. L.; Fischer, P. A.; Sigal, N. H. *J. Immunol.* 1990, 144, 1418-1424; Bierer, B. E.; Schreiber, S. L.; Burakoff, S. J. *Eur. J. Immunol.* 1991, 21, 439-445; Fretz, H.; Albers, M. W.; Galat, A.; Standaert, R. F.; Lane, W. S.; Burakoff, S. J.; Bierer, B. E.; Schreiber, S. L. *J. Am. Chem. Soc.* 1991, 113, 1409-1411). Recently it has been discovered that the rapamycin/FKBP-12 complex binds to yet another protein, which is distinct from calcineurin, the protein that the FK-506/FKBP-12 complex inhibits (Brown, E. J.; Albers, M. W.; Shin, T. B.; Ichikawa, K.; Keith, C. T.; Lane, W. S.; Schreiber, S. L. *Nature* 1994, 369, 756-758; Sabatini, D. M.; Erdjument-Bromage, H.; Lui, M.; Tempest, P.; Snyder, S. H. *Cell,* 1994, 78, 35-43).

Percutaneous transluminal coronary angioplasty (PTCA) was developed by Andreas Gruntzig in the 1970's. The first canine coronary dilation was performed on Sep. 24, 1975; studies showing the use of PTCA were presented at the annual meetings of the American Heart Association the following year. Shortly thereafter, the first human patient was studied in Zurich, Switzerland, followed by the first American human patients in San Francisco and New York. While this procedure changed the practice of interventional cardiology with respect to treatment of patients with obstructive coronary artery disease, the procedure did not provide long-term solutions. Patients received only temporary abatement of the chest pain associated with vascular occlusion; repeat procedures were often necessary. It was determined that the existence of restenotic lesions severely limited the usefulness of the new procedure. In the late 1980's, stents were introduced to maintain vessel patency after angioplasty. Stenting is involved in 90% of angioplasty performed today. Before the introduction of stents, the rate of restenosis ranged from 30% to 50% of the patients who were treated with balloon angioplasty. The recurrence rate after dilatation of in-stent restenosis may be as high as 70% in selected patient subsets, while the angiographic restenosis rate in de novo stent placement is about 20%. Placement of the stent reduced the restenosis rate to 15% to 20%. This percentage likely represents the best results obtainable with purely mechanical stenting. The restenosis lesion is caused primarily by neointimal hyperplasia, which is distinctly different from atherosclerotic disease both in time-course and in histopathologic appearance. Restenosis is a healing process of damaged coronary arterial walls, with neointimal tissue impinging significantly on the vessel lumen. Vascular brachytherapy appears to be efficacious against in-stent restenosis lesions. Radiation, however, has limitations of practicality and expense, and lingering questions about safety and durability.

Accordingly, it is desired to reduce the rate of restenosis by at least 50% of its current level. It is for this reason that a major effort is underway by the interventional device community to fabricate and evaluate drug-eluting stents. Such devices could have many advantages if they were successful, principally since such systems would need no auxiliary therapies, either in the form of peri-procedural techniques or chronic oral pharmacotherapy.

BRIEF SUMMARY OF THE INVENTION

The invention relates to compounds and methods for treating and preventing of restenosis. More particularly, the invention relates to prodrugs of rapamycin and methods of treatment employing the same.

Embodiments of the invention include the prodrugs of the following compound

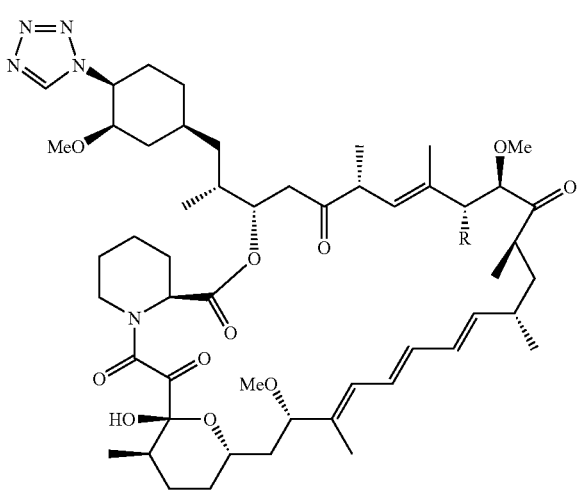

In this structure, $R=R^1C(O)R^2R^3$ or $R^1C(S)R^2R^3$, where $R^1=O$ or S; $R^2=$nothing, O, N, S, or one of various alkyl, alkenyl, alkynyl, heterocycle, or aryl groups; and $R^3=$nothing or one of various alkyl, alkenyl, alkynyl, heterocycle, or aryl groups. The various alkyl, alkenyl, alkynyl, heterocycles, aryl groups can be substituted or unsubstituted.

The purpose and advantages of embodiments of the invention will be set forth in and will become apparent from the description that follows, as well as will be learned by practice of the invention.

Additional advantages of the invention will be realized and attained by the methods and systems particularly pointed out in the written description and claims hereof, as well as from the appended drawings.

Another aspect of the invention, there is provided the manufacture of the prodrug compounds and methods for inhibiting, treating and/or preventing diseases including, but not limited to, restenosis, autoimmune diseases, post-transplant-tissue transplant rejections, fungal growth, or cancer utilizing the prodrugs described herein.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments which are illustrated schematically in the accompanying drawings and in the appended claims.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 2 is a side view in elevation showing a stent suitable for use in this invention.

FIG. 3A is a cross-sectional view of a vessel segment in which was placed a stent coated with a polymer only.

FIG. 3B is a cross-sectional view of a vessel segment in which was placed a stent coated with a polymer plus drug.

DETAILED DESCRIPTION OF THE INVENTION

Definition of Terms

Figure 1:
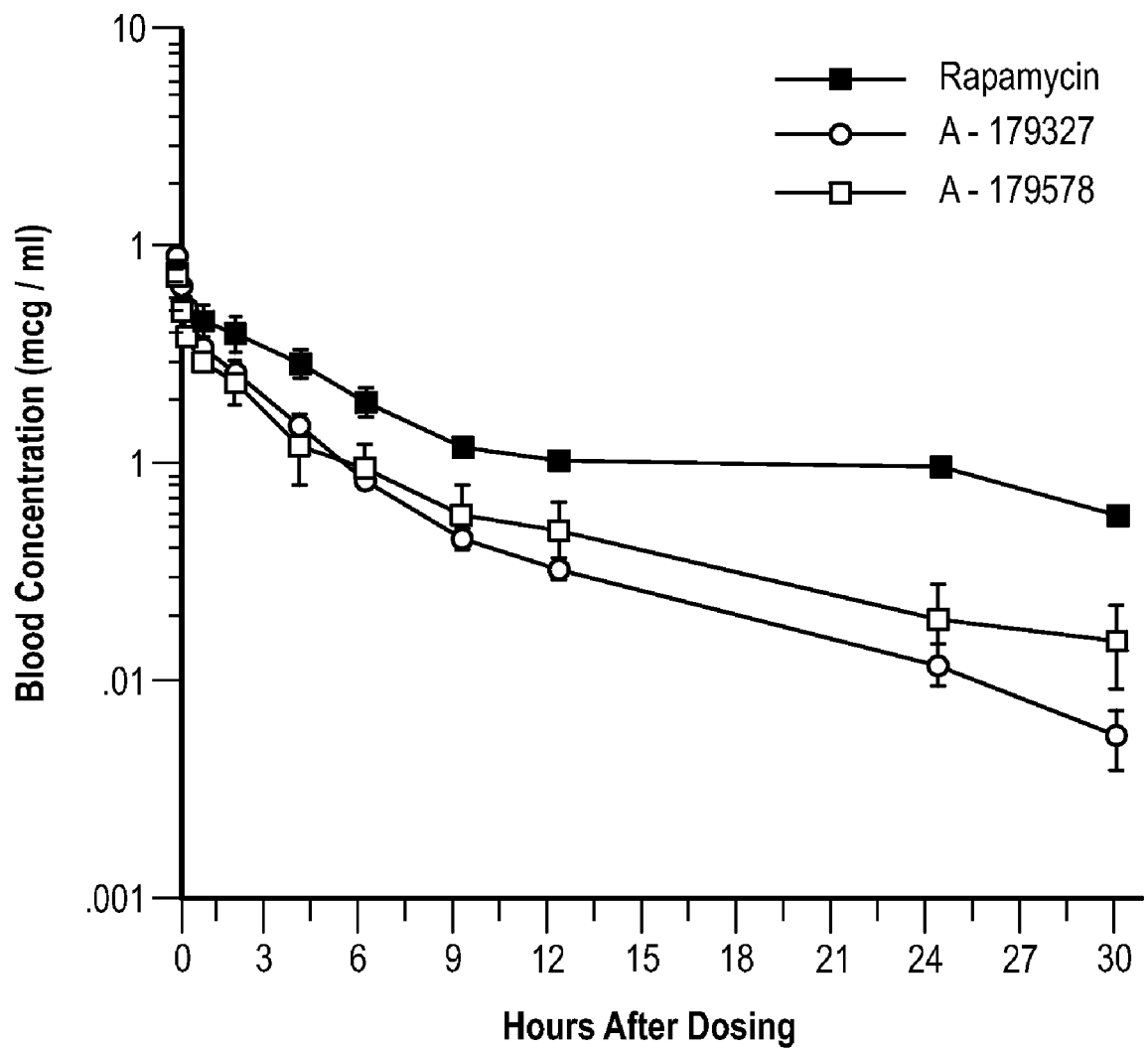
FIG. 1 shows blood concentrations ±SEM (n=3) of tetrazole-containing rapamycin analogs dosed in monkey.

The term "prodrug," as used herein, refers to compounds which are rapidly transformed in vivo to the parent compound of the above formula, for example, by hydrolysis in blood. A thorough discussion is provided by T. Higuchi and V. Stella, "Pro-drugs as Novel Delivery systems," Vol. 14 of the A.C.S. Symposium Series, and in Edward B. Roche, ed., "Bioreversible Carriers in Drug Design," American Pharmaceutical Association and Pergamon Press, 1987, both of which are incorporated herein by reference.

The term "pharmaceutically acceptable prodrugs", as used herein, refers to those prodrugs of the compounds of the present invention which are, within the scope of sound medical judgment, suitable for use in contact with the tissues of humans and lower mammals without undue toxicity, irritation, and allergic response, are commensurate with a reasonable benefit/risk ratio, and are effective for their intended use, as well as the zwitterionic forms, where possible, of the compounds of the invention. Other pharmaceutically acceptable prodrugs of this invention are prodrug esters of the C-31 hydroxyl group of compounds of this invention.

The term "prodrug esters," as used herein, refers to any of several ester-forming groups that are hydrolyzed under physiological conditions. Examples of prodrug ester groups include acetyl, propiopyl, pivaloyl, pivaloyloxymethyl, acetoxymethyl, phthalidyl, methoxymethyl, indanyl, and the like, as well as ester groups derived from the coupling of naturally or unnaturally-occurring amino acids to the C-31 hydroxyl group of compounds of this invention.

The term "supporting structure" means a framework that is capable of containing or supporting a pharmaceutically acceptable carrier or excipient, which carrier or excipient may contain a therapeutic agent, e.g., a drug or another compound. The supporting structure is typically formed of metal or a polymeric material.

EMBODIMENTS

Embodiments of the invention include the prodrugs of the following compound

Embodiments of the invention include the prodrugs of the following compound.

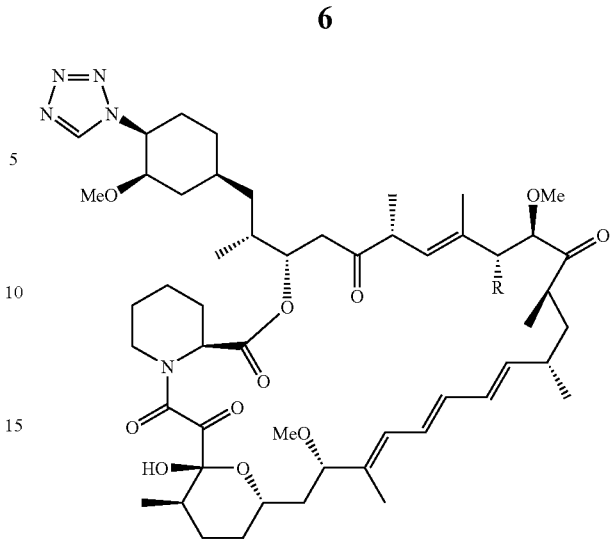

In this structure, $R=R^1C(O)R^2R^3$ or $R^1C(S)R^2R^3$, where $R^1=O$ or S; $R^2=$nothing, O, N, S, or one of various alkyl, alkenyl, alkynyl, heterocycle, or aryl groups; and $R^3=$nothing or one of various alkyl, alkenyl, alkynyl, heterocycle, or aryl groups. The various alkyl, alkenyl, alkynyl, heterocycles, aryl groups can be substituted or unsubstituted.

Another aspect of the invention, there is provided the manufacture of the prodrug compounds and methods for inhibiting, treating and/or preventing diseases including, but not limited to, restenosis, autoimmune diseases, post-transplant-tissue transplant rejections, fungal growth, or cancer utilizing the prodrugs described herein.

In one embodiment of the invention is a compound of formula

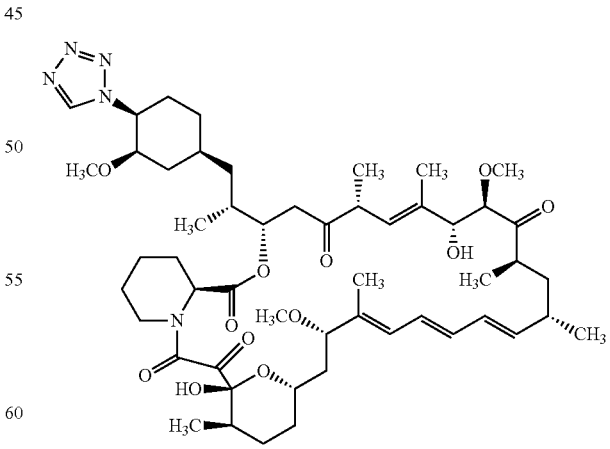

In another embodiment of the invention is a compound of formula

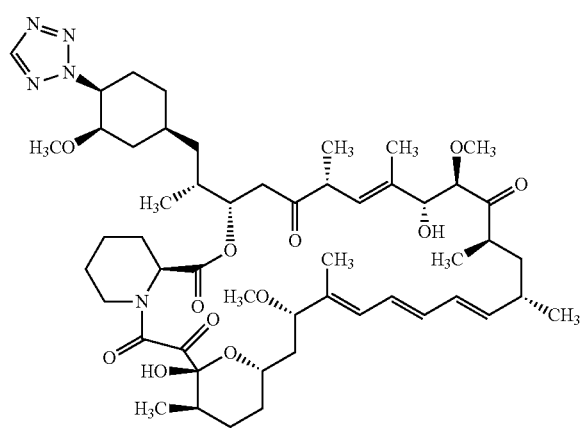

Preparation of Compounds of this Invention

The compounds and processes of the present invention will be better understood in connection with the following synthetic schemes which illustrate the methods by which the compounds of the invention may be prepared.

The compounds of this invention may be prepared by a variety of synthetic routes. A representative procedure is shown in Scheme 1.

Scheme 1

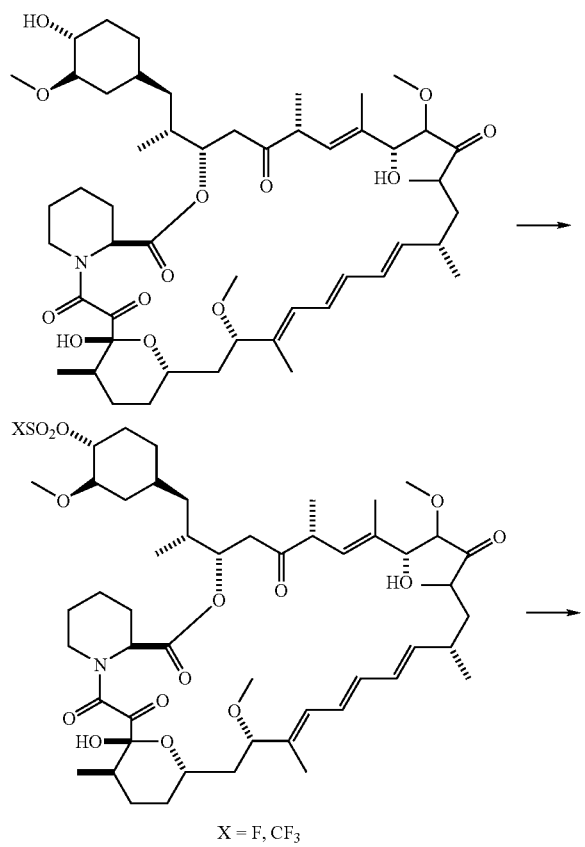

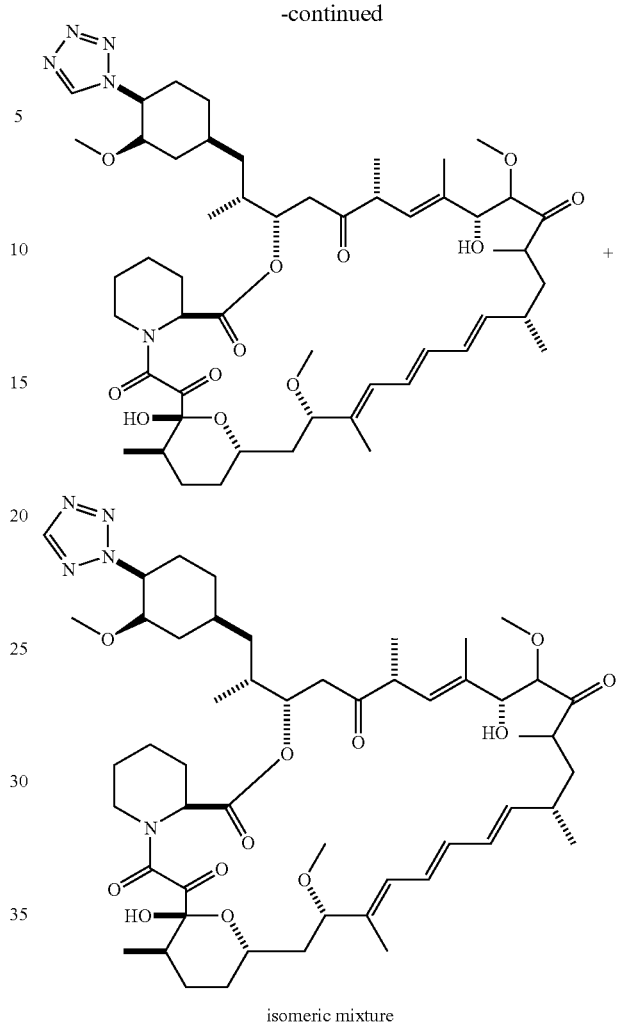

isomeric mixture

As shown in Scheme 1, conversion of the C-42 hydroxyl of rapamycin to a trifluoromethanesulfonate or fluorosulfonate leaving group provided A. Displacement of the leaving group with tetrazole in the presence of a hindered, non-nucleophilic base, such as 2,6-lutidine, or, preferably, diisopropylethyl amine provided isomers B and C, which were separated and purified by flash column chromatography.

Synthetic Methods

The foregoing may be better understood by reference to the following examples which illustrate the methods by which the compounds of the invention may be prepared and are not intended to limit the scope of the invention as defined in the appended claims.

Example 1

42-(2-tetrazolyl)-rapamycin (less polar isomer)

Example 1A

A solution of rapamycin (100 mg, 0.11 mmol) in dichloromethane (0.6 mL) at −78° C. under a nitrogen atmosphere was treated sequentially with 2,6-lutidine (53 uL, 0.46 mmol, 4.3 eq.) and trifluoromethanesulfonic anhydride (37 uL, 0.22 mmol), and stirred thereafter for 15 minutes, warmed to room temperature and eluted through a pad of silica gel (6 mL) with diethyl ether. Fractions containing the triflate were pooled and concentrated to provide the designated compound as an amber foam.

Example 1B 42-(2-tetrazolyl)-rapamycin (less polar isomer)

A solution of Example 1A in isopropyl acetate (0.3 mL) was treated sequentially with diisopropylethylamine (87 µL, 0.5 mmol) and 1H-tetrazole (35 mg, 0.5 mmol), and thereafter stirred for 18 hours. This mixture was partitioned between water (10 mL) and ether (10 mL). The organics were washed with brine (10 mL) and dried (Na2SO4). Concentration of the organics provided a sticky yellow solid which was purified by chromatography on silica gel (3.5 g, 70-230 mesh) eluting with hexane (10 mL), hexane:ether (4:1 (10 mL), 3:1 (10 mL), 2:1 (10 mL), 1:1 (10 mL)), ether (30 mL), hexane:acetone (1:1 (30 mL)). One of the isomers was collected in the ether fractions.

MS (ESI) m/e 966 (M)−;

Example 2

42-(1-tetrazolyl)-rapamycin (more polar isomer)

Example 2A

Collection of the slower moving band from the chromatography column using the hexane:acetone (1:1) mobile phase in Example 1B provided the designated compound.

MS (ESI) m/e 966 (M)−.

In Vitro Assay of Biological Activity

The immunosuppressant activity of the compounds of the present invention was compared to rapamycin and two rapamycin analogs: 40-epi-N-[2'-pyridone]-rapamycin and 40-epi-N-[4'-pyridone]-rapamycin, both disclosed in U.S. Pat. No. 5,527,907. The activity was determined using the human mixed lymphocyte reaction (MLR) assay described by Kino, T. et al. in Transplantation Proceedings, XIX(5):36-39, Suppl. 6 (1987). The results of the assay demonstrate that the compounds of the invention are effective immunomodulators at nanomolar concentrations, as shown in Table 1.

TABLE 1

| Example | Human MLR IC50 ± S.E.M.(nM) |
|---|---|
| Rapamycin | 0.91 ± 0.36 |
| 2-pyridone | 12.39 ± 5.3 |
| 4-pyridone | 0.43 ± 0.20 |
| Example 1 | 1.70 ± 0.48 |
| Example 2 | 0.66 ± 0.19 |

The pharmacokinetic behaviors of Example 1 and Example 2 were characterized following a single 2.5 mg/kg intravenous dose in cynomolgus monkey (n=3 per group). Each compound was prepared as 2.5 mg/mL solution in a 20% ethanol:30% propylene glycol:2% cremophor EL:48% dextrose 5% in water vehicle. The 1 mL/kg intravenous dose was administered as a slow bolus (~1-2 minutes) in a saphenous vein of the monkeys. Blood samples were obtained from a femoral artery or vein of each animal prior to dosing and 0.1 (IV only), 0.25, 0.5, 1, 1.5, 2, 4, 6, 9, 12, 24, and 30 hours after dosing. The EDTA preserved samples were thoroughly mixed and extracted for subsequent analysis.

An aliquot of blood (1.0 mL) was hemolyzed with 20% methanol in water (0.5 ml) containing an internal standard. The hemolyzed samples were extracted with a mixture of ethyl acetate and hexane (1:1 (v/v), 6.0 mL). The organic layer was evaporated to dryness with a stream of nitrogen at room temperature. Samples were reconstituted in methanol:water (1:1, 150 µL). The title compounds (50 µL injection) were separated from contaminants using reverse phase HPLC with UV detection. Samples were kept cool (4° C.) through the run. All samples from each study were analyzed as a single batch on the HPLC.

Area under the curve (AUC) measurements of Example 1, Example 2 and the internal standard were determined using the Sciex MacQuan™ software. Calibration curves were derived from peak area ratio (parent drug/internal standard) of the spiked blood standards using least squares linear regression of the ratio versus the theoretical concentration. The methods were linear for both compounds over the range of the standard curve (correlation >0.99) with an estimated quantitation limit of 0.1 ng/mL. The maximum blood concentration (CMAX) and the time to reach the maximum blood concentration (TMAX) were read directly from the observed blood concentration-time data. The blood concentration data were submitted to multi-exponential curve fitting using CSTRIP to obtain estimates of pharmacokinetic parameters. The estimated parameters were further defined using NONLIN84. The area under the blood concentration-time curve from 0 to t hours (last measurable blood concentration time point) after dosing (AUC0-t) was calculated using the linear trapezoidal rule for the blood-time profiles. The residual area extrapolated to infinity, determined as the final measured blood concentration (Ct) divided by the terminal elimination rate constant ($\beta$), and added to AUC0-t to produce the total area under the curve (AUC0-t).

As shown in FIG. 1 and Table 2, both Example 1 and Example 2 had a surprisingly substantially shorter terminal elimination half-life (t1/2) when compared to rapamycin. Thus, only the compounds of the invention provide both sufficient efficacy (Table 1) and a shorter terminal half-life (Table 2).

TABLE 2

| Compound | AUC ng · hr/mL | t½ (hours) |
|---|---|---|
| Rapamycin | 6.87 | 16.7 |
| 2-pyridone | 2.55 | 2.8 |
| 4-pyridone | 5.59 | 13.3 |
| Example 1 | 2.35 | 5.0 |
| Example 2 | 2.38 | 6.9 |

Methods of Treatment

The compounds of the invention, including but not limited to those specified in the examples, possess immunomodulatory activity in mammals (especially humans). As immunosuppressants, the compounds of the present invention are useful for the treatment and prevention of immune-mediated diseases such as the resistance by transplantation of organs or tissue such as heart, kidney, liver, medulla ossium, skin, cornea, lung, pancreas, intestinum tenue, limb, muscle, nerves, duodenum, small-bowel, pancreatic-islet-cell, and the like; graft-versus-host diseases brought about by medulla ossium transplantation; autoimmune diseases such as rheumatoid arthritis, systemic lupus erythematosus, Hashimoto's thyroiditis, multiple sclerosis, myasthenia gravis, Type I diabetes, uveitis, allergic encephalomyelitis, glomerulonephritis, and the like. Further uses include the treatment and prophylaxis of inflammatory and hyperproliferative skin diseases and cutaneous manifestations of immunologically-mediated illnesses, such as psoriasis, atopic dermatitis, contact dermatitis and further eczematous dermatitises, seborrhoeis dermatitis, lichen planus, pemphigus, bullous pemphigoid, epidermolysis bullosa, urticaria, angioedemas, vasculitides, erythemas, cutaneous eosinophilias, lupus erythematosus, acne and alopecia greata; various eye diseases (autoimmune and otherwise) such as keratoconjunctivitis, vernal conjunctivitis, uveitis associated with Behcet's disease, keratitis, herpetic keratitis, conical cornea, dystrophia epithelialis corneae, corneal leukoma, and ocular pemphigus. In addition reversible obstructive airway disease, which includes conditions such as asthma (for example, bronchial asthma, allergic asthma, intrinsic asthma, extrinsic asthma and dust asthma), particularly chronic or inveterate asthma (for example, late asthma and airway hyper-responsiveness), bronchitis, allergic rhinitis, and the like are targeted by compounds of this invention. Inflammation of mucosa and blood vessels such as gastric ulcers, vascular damage caused by ischemic diseases and thrombosis. Moreover, hyperproliferative vascular diseases such as intimal smooth muscle cell hyperplasia, restenosis and vascular occlusion, particularly following biologically- or mechanically-mediated vascular injury, could be treated or prevented by the compounds of the invention.

The compounds or drugs described herein can be applied to stents that have been coated with a polymeric compound. Incorporation of the compound or drug into the polymeric coating of the stent can be carried out by dipping the polymer-coated stent into a solution containing the compound or drug for a sufficient period of time (such as, for example, five minutes) and then drying the coated stent, preferably by means of air drying for a sufficient period of time (such as, for example, 30 minutes). The polymer-coated stent containing the compound or drug can then be delivered to the coronary vessel by deployment from a balloon catheter. In addition to stents, other devices that can be used to introduce the drugs of this invention to the vasculature include, but are not limited to, grafts, catheters, and balloons. In addition, other compounds or drugs that can be used in lieu of the drugs of this invention include, but are not limited to, A-94507 and SDZ RAD (a.k.a. Everolimus).

The compounds described herein for use in polymer-coated stents can be used in combination with other pharmacological agents. The pharmacologic agents that would, in combination with the compounds of this invention, be most effective in preventing restenosis can be classified into the categories of anti-proliferative agents, anti-platelet agents, anti-inflammatory agents, anti-thrombotic agents, and thrombolytic agents. These classes can be further sub-divided. For example, anti-proliferative agents can be anti-mitotic. Anti-mitotic agents inhibit or affect cell division, whereby processes normally involved in cell division do not take place. One sub-class of anti-mitotic agents includes vinca alkaloids. Representative examples of vinca alkaloids include, but are not limited to, vincristine, paclitaxel, etoposide, nocodazole, indirubin, and anthracycline derivatives, such as, for example, daunorubicin, daunomycin, and plicamycin. Other sub-classes of anti-mitotic agents include anti-mitotic alkylating agents, such as, for example, tauromustine, bofumustine, and fotemustine, and anti-mitotic metabolites, such as, for example, methotrexate, fluorouracil, 5-bromodeoxyuridine, 6-azacytidine, and cytarabine. Anti-mitotic alkylating agents affect cell division by covalently modifying DNA, RNA, or proteins, thereby inhibiting DNA replication, RNA transcription, RNA translation, protein synthesis, or combinations of the foregoing.

Anti-platelet agents are therapeutic entities that act by (1) inhibiting adhesion of platelets to a surface, typically a thrombogenic surface, (2) inhibiting aggregation of platelets, (3) inhibiting activation of platelets, or (4) combinations of the foregoing. Activation of platelets is a process whereby platelets are converted from a quiescent, resting state to one in which platelets undergo a number of morphologic changes induced by contact with a thrombogenic surface. These changes include changes in the shape of the platelets, accompanied by the formation of pseudopods, binding to membrane receptors, and secretion of small molecules and proteins, such as, for example, ADP and platelet factor 4. Anti-platelet agents that act as inhibitors of adhesion of platelets include, but are not limited to, eptifibatide, tirofiban, RGD (Arg-Gly-Asp)-based peptides that inhibit binding to gpIIbIIIa or $\alpha v\beta 3$, antibodies that block binding to gpIIaIIIb or $\alpha v\beta 3$, anti-P-selectin antibodies, anti-E-selectin antibodies, compounds that block P-selectin or E-selectin binding to their respective ligands, saratin, and anti-von Willebrand factor antibodies. Agents that inhibit ADP-mediated platelet aggregation include, but are not limited to, disagregin and cilostazol.

Anti-inflammatory agents can also be used. Examples of these include, but are not limited to, prednisone, dexamethasone, hydrocortisone, estradiol, fluticasone, clobetasol, and non-steroidal anti-inflammatories, such as, for example, acetaminophen, ibuprofen, naproxen, and sulindac. Other examples of these agents include those that inhibit binding of cytokines or chemokines to the cognate receptors to inhibit pro-inflammatory signals transduced by the cytokines or the chemokines. Representative examples of these agents include, but are not limited to, anti-IL1, anti-IL2, anti-IL3, anti-IL4, anti-IL8, anti-IL15, anti-IL18, anti-GM-CSF, and anti-TNF antibodies.

Anti-thrombotic agents include chemical and biological entities that can intervene at any stage in the coagulation pathway. Examples of specific entities include, but are not limited to, small molecules that inhibit the activity of factor Xa. In addition, heparinoid-type agents that can inhibit both FXa and thrombin, either directly or indirectly, such as, for example, heparin, heparin sulfate, low molecular weight heparins, such as, for example, the compound having the trademark Clivarin®, and synthetic oligosaccharides, such as, for example, the compound having the trademark Arixtra®. Also included are direct thrombin inhibitors, such as, for example, melagatran, ximelagatran, argatroban, inogatran, and peptidomimetics of binding site of the Phe-Pro-Arg fibrinogen substrate for thrombin. Another class of anti-thrombotic agents that can be delivered are factor VII/VIIa inhibitors, such as, for example, anti-factor VII/VIIa antibodies, rNAPc2, and tissue factor pathway inhibitor (TFPI).

Thrombolytic agents, which may be defined as agents that help degrade thrombi (clots), can also be used as adjunctive agents, because the action of lysing a clot helps to disperse platelets trapped within the fibrin matrix of a thrombus. Representative examples of thrombolytic agents include, but are not limited to, urokinase or recombinant urokinase, pro-urokinase or recombinant pro-urokinase, tissue plasminogen activator or its recombinant form, and streptokinase.

Other drugs that can be used in combination with the compounds of this invention are cytotoxic drugs, such as, for example, apoptosis inducers, such as TGF, and topoisomerase inhibitors, such as, 10-hydroxycamptothecin, irinotecan, and doxorubicin. Other classes of drugs that can be used in combination with the compounds of this invention are drugs that inhibit cell de-differentiation and cytostatic drugs.

Other agents that can be used in combination with the compounds of this invention include fenofibrate, batimistat, antagonists of the endothelin-A receptor, such as, for example, darusentan, and antagonists of the αvβ3 integrin receptor.

When used in the present invention, the coating can comprise any polymeric material in which the therapeutic agent, i.e., the drug, is substantially soluble. The purpose of the coating is to serve as a controlled release vehicle for the therapeutic agent or as a reservoir for a therapeutic agent to be delivered at the site of a lesion. The coating can be polymeric and can further be hydrophilic, hydrophobic, biodegradable, or non-biodegradable. The material for the polymeric coating can be selected from the group consisting of polyacrylates, polymethacrylates, polycarboxylic acids, cellulosic polymers, gelatin, polyvinylpyrrolidone, maleic anhydride polymers, polyamides, polyvinyl alcohols, polyethylene oxides, glycosaminoglycans, polysaccharides, polyesters, polyurethanes, silicones, polyorthoesters, polyanhydrides, polycarbonates, polypropylenes, polylactic acids, polyglycolic acids, polycaprolactones, polyhydroxybutyrate valerates, polyacrylamides, polyethers, and mixtures and copolymers of the foregoing. Coatings prepared from polymeric dispersions such as polyurethane dispersions (BAYHYDROL, etc.) and acrylic acid latex dispersions can also be used with the therapeutic agents of the present invention.

Biodegradable polymers that can be used in this invention include polymers such as poly(L-lactic acid), poly(DL-lactic acid), polycaprolactone, poly(hydroxy butyrate), polyglycolide, poly(diaxanone), poly(hydroxy valerate), polyorthoester; copolymers such as poly(lactide-co-glycolide), polyhydroxy(butyrate-co-valerate), polyglycolide-co-trimethylene carbonate; polyanhydrides; polyphosphoester; polyphosphoester-urethane; polyamino acids; polycyanoacrylates; biomolecules such as fibrin, fibrinogen, cellulose, starch, collagen and hyaluronic acid; and mixtures of the foregoing. Biostable materials that are suitable for use in this invention include polymers such as polyurethane, silicones, polyesters, polyolefins, polyamides, polycaprolactam, polyimide, polyvinyl chloride, polyvinyl methyl ether, polyvinyl alcohol, acrylic polymers and copolymers, polyacrylonitrile, polystyrene copolymers of vinyl monomers with olefins (such as styrene acrylonitrile copolymers, ethylene methyl methacrylate copolymers, ethylene vinyl acetate), polyethers, rayons, cellulosics (such as cellulose acetate, cellulose nitrate, cellulose propionate, etc.), parylene and derivatives thereof, and mixtures and copolymers of the foregoing.

Other polymers that can be used in embodiments of this invention include, but are not limited to, those having MPC subunit including poly(MPCw:LAMx:HPMAy:TSMAz) where w, x, y, and z represent the molar ratios of monomers used in the feed for preparing the polymer and MPC represents the unit 2-methacryoyloxyethylphosphorylcholine, LMA represents the unit lauryl methacrylate, HPMA represents the unit 2-hydroxypropyl methacrylate, and TSMA represents the unit 3-trimethoxysilylpropyl methacrylate. The drug-impregnated stent can be used to maintain patency of a coronary artery previously occluded by thrombus and/or atherosclerotic plaque. The delivery of an anti-proliferative agent reduces the rate of in-stent restenosis.

Other treatable conditions include but are not limited to ischemic bowel diseases, inflammatory bowel diseases, necrotizing enterocolitis, intestinal inflammations/allergies such as Coeliac diseases, proctitis, eosinophilic gastroenteritis, mastocytosis, Crohn's disease and ulcerative colitis; nervous diseases such as multiple myositis, Guillain-Barre syndrome, Meniere's disease, polyneuritis, multiple neuritis, mononeuritis and radiculopathy; endocrine diseases such as hyperthyroidism and Basedow's disease; hematic diseases such as pure red cell aplasia, aplastic anemia, hypoplastic anemia, idiopathic thrombocytopenic purpura, autoimmune hemolytic anemia, agranulocytosis, pernicious anemia, megaloblastic anemia and anerythroplasia; bone diseases such as osteoporosis; respiratory diseases such as sarcoidosis, fibroid lung and idiopathic interstitial pneumonia; skin disease such as dermatomyositis, leukoderma vulgaris, ichthyosis vulgaris, photoallergic sensitivity and cutaneous T cell lymphoma; circulatory diseases such as arteriosclerosis, atherosclerosis, aortitis syndrome, polyarteritis nodosa and myocardosis; collagen diseases such as scleroderma, Wegener's granuloma and Sjogren's syndrome; adiposis; eosinophilic fasciitis; periodontal disease such as lesions of gingiva, periodontium, alveolar bone and substantia ossea dentis; nephrotic syndrome such as glomerulonephritis; male pattern aleopecia or alopecia senilis by preventing epilation or providing hair germination and/or promoting hair generation and hair growth; muscular dystrophy; Pyoderma and Sezary's syndrome; Addison's disease; active oxygen-mediated diseases, as for example organ injury such as ischemia-reperfusion injury of organs (such as heart, liver, kidney and digestive tract) which occurs upon preservation, transplantation or ischemic disease (for example, thrombosis and cardiac infarction); intestinal diseases such as endotoxin-shock, pseudomembranous colitis and colitis caused by drug or radiation; renal diseases such as ischemic acute renal insufficiency and chronic renal insufficiency; pulmonary diseases such as toxinosis caused by lung-oxygen or drug (for example, paracort and bleomycins), lung cancer and pulmonary emphysema; ocular diseases such as cataracta, siderosis, retinitis, pigmentosa, senile macular degeneration, vitreal scarring and corneal alkali burn; dermatitis such as erythema multiforme, linear IgA ballous dermatitis and cement dermatitis; and others such as gingivitis, periodontitis, sepsis, pancreatitis, diseases caused by environmental pollution (for example, air pollution), aging, carcinogenesis, metastasis of carcinoma and hypobaropathy; diseases caused by histamine or leukotriene-C4 release; Behcet's disease such as intestinal-, vasculo- or neuro-Behcet's disease, and also Behcet's which affects the oral cavity, skin, eye, vulva, articulation, epididymis, lung, kidney and so on. Furthermore, the compounds of the invention are useful for the treatment and prevention of hepatic disease such as immunogenic diseases (for example, chronic autoimmune liver diseases such as autoimmune hepatitis, primary biliary cirrhosis and sclerosing cholangitis), partial liver resection, acute liver necrosis (e.g. necrosis caused by toxin, viral hepatitis, shock or anoxia), B-virus hepatitis, non-A/non-B hepatitis, cirrhosis (such as alcoholic cirrhosis) and hepatic failure such as fulminant hepatic failure, late-onset hepatic failure and "acute-on-chronic" liver failure (acute liver failure on chronic liver diseases), and moreover are useful for various diseases because of their useful activity such as augmentation of chemotherapeutic effect, cytomegalovirus infection, particularly HCMV infection, anti-inflammatory activity, sclerosing and fibrotic diseases such as nephrosis, scleroderma, pulmonary fibrosis, arteriosclerosis, congestive heart failure, ventricular hypertrophy, post-surgical adhesions and scarring, stroke, myocardial infarction and injury associated with ischemia and reperfusion, and the like.

Additionally, compounds of the invention possess FK-506 antagonistic properties. The compounds of the present invention may thus be used in the treatment of immunodepression or a disorder involving immunodepression. Examples of disorders involving immunodepression include AIDS, cancer, fungal infections, senile dementia, trauma (including wound healing, surgery and shock) chronic bacterial infection, and certain central nervous system disorders. The immunodepression to be treated may be caused by an overdose of an immunosuppressive macrocyclic compound, for example derivatives of 12-(2-cyclohexyl-1-methylvinyl)-13,19,21,27-tetramethyl-11,28-dioxa-4-azatricyclo[22.3.1.0 4,9]octacos-18-ene such as FK-506 or rapamycin. The overdosing of such medicants by patients is quite common upon their realizing that they have forgotten to take their medication at the prescribed time and can lead to serious side effects.

The ability of the compounds of the invention to treat proliferative diseases can be demonstrated according to the methods described in Bunchman E T and C A Brookshire, Transplantation Proceed. 23 967-968 (1991); Yamagishi, et al., Biochem. Biophys. Res. Comm. 191 840-846 (1993); and Shichiri, et al., J. Clin. Invest. 87 1867-1871 (1991). Proliferative diseases include smooth muscle proliferation, systemic sclerosis, cirrhosis of the liver, adult respiratory distress syndrome, idiopathic cardiomyopathy, lupus erythematosus, diabetic retinopathy or other retinopathies, psoriasis, scleroderma, prostatic hyperplasia, cardiac hyperplasia, restenosis following arterial injury or other pathologic stenosis of blood vessels. In addition, these compounds antagonize cellular responses to several growth factors, and therefore possess antiangiogenic properties, making them useful agents to control or reverse the growth of certain tumors, as well as fibrotic diseases of the lung, liver, and kidney.

Aqueous liquid compositions of the present invention are particularly useful for the treatment and prevention of various diseases of the eye such as autoimmune diseases (including, for example, conical cornea, keratitis, dysophia epithelialis corneae, leukoma, Mooren's ulcer, sclevitis and Graves' opthalmopathy) and rejection of corneal transplantation.

When used in the above or other treatments, a therapeutically effective amount of one of the compounds of the present invention may be employed in pure form or, where such forms exist, in pharmaceutically acceptable salt, ester or prodrug form. Alternatively, the compound may be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.01 to about 10 mg/kg/day. For purposes of oral administration, more preferable doses may be in the range of from about 0.001 to about 3 mg/kg/day. For the purposes of local delivery from a stent, the daily dose that a patient will receive depends on the length of the stent. For example, a 15 mm coronary stent may contain a drug in an amount ranging from about 1 to about 120 micrograms and may deliver that drug over a time period ranging from several hours to several weeks. If desired, the effective daily dose may be divided into multiple doses for purposes of administration; consequently, single dose compositions may contain such amounts or sub-multiples thereof to make up the daily dose. Topical administration may involve doses ranging from 0.001 to 3% mg/kg/day, depending on the site of application.

Pharmaceutical Compositions

The pharmaceutical compositions of the present invention comprise a compound of the invention and a pharmaceutically acceptable carrier or excipient, which may be administered orally, rectally, parenterally, intracisternally, intravaginally, intraperitoneally, topically (as by powders, ointments, drops or transdermal patch), buccally, as an oral or nasal spray, or locally, as in a stent placed within the vasculature. The phrase "pharmaceutically acceptable carrier" means a non-toxic solid, semi-solid or liquid filler, diluent, encapsulating material or formulation auxiliary of any type. The term "parenteral," as used herein, refers to modes of administration which include intravenous, intraarterial, intramuscular, intraperitoneal, intrasternal, subcutaneous and intraarticular injection, infusion, and placement, such as, for example, in vasculature.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft, semi-solid and hard-filled gelatin capsules or liquid-filled capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Those embedding compositions containing a drug can be placed on medical devices, such as stents, grafts, catheters, and balloons.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically acceptable inert carrier comprising particles having a size, for example, of up to 100 micrometers in diameter. Suitable inert carriers include sugars such as lactose. Desirably, at least 95% by weight of the particles of the active ingredient have an effective particle size in the range of 0.01 to 10 micrometers. Compositions for topical use on the skin also include ointments, creams, lotions, and gels.

Alternatively, the composition may be pressurized and contain a compressed gas, such as nitrogen or a liquified gas propellant. The liquified propellant medium and indeed the total composition is preferably such that the active ingredient does not dissolve therein to any substantial extent. The pressurized composition may also contain a surface active agent. The surface active agent may be a liquid or solid non-ionic surface active agent or may be a solid anionic surface active agent. It is preferred to use the solid anionic surface active agent in the form of a sodium salt.

A further form of topical administration is to the eye, as for the treatment of immune-mediated conditions of the eye such as autoimmune diseases, allergic or inflammatory conditions, and corneal transplants. The compound of the invention is delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically acceptable ophthalmic vehicle may, for example, be an ointment, vegetable oil or an encapsulating material.

Compositions for rectal or vaginal administration are preferably suppositories or retention enemas which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., Methods in Cell Biology, Volume XIV, Academic Press, New York, N.Y. (1976), p. 33 et seq.

Compounds of the present invention may also be coadministered with one or more immunosuppressant agents. The immunosuppressant agents within the scope of this invention include, but are not limited to, IMURAN® azathioprine sodium, brequinar sodium, SPANIDIN® gusperimus trihydrochloride (also known as deoxyspergualin), mizoribine (also known as bredinin), CELLCEPT® mycophenolate mofetil, NEORAL® Cylosporin A (also marketed as different formulation of Cyclosporin A under the trademark SANDIMMUNE®), PROGRAF® tacrolimus (also known as FK-506), sirolimus and RAPAMUNE®, leflunomide (also known as HWA-486), glucocorticoids, such as prednisolone and its derivatives, antibody therapies such as orthoclone (OKT3) and Zenapax®, and antithymyocyte globulins, such as thymoglobulins.

Example 3

The purpose of this example was to determine the effects of a rapamycin analog on neointimal formation in porcine coronary arteries containing stents. This example illustrates that the rapamycin analog A-179578, when compounded and delivered from the Biocompatibles BiodiviYsio PC Coronary stent favorably affects neointimal hyperplasia and lumen size in porcine coronary arteries. This finding suggests that such a combination may be of substantial clinical benefit if properly applied in humans by limiting neointimal hyperplasia.

The agent A-179578 is a rapamycin analog. The study set forth in this example was designed to assess the ability of the rapamycin analog A-179578 to reduce neointimal hyperplasia in a porcine coronary stent model. Efficacy of A-179578 in this model would suggest its clinical potential for the limitation and treatment of coronary restenosis in stents following percutaneous revascularization. The domestic swine was used because this model appears to yield results comparable to other investigations seeking to limit neointimal hyperplasia in human subjects.

The example tested A-179578 eluted from coronary stents placed in juvenile farm pigs, and compared these results with control stents. The control stents are polymer-coated without drugs. This is important, for the polymer itself must not stimulate neointimal hyperplasia to a substantial degree. As the eluted drug disappears, an inflammatory response to the polymer could conceivably result in a late "catch-up phenomenon" where the restenosis process is not stopped, but instead slowed. This phenomenon would result in restenosis at late dates in human subjects.

Stents were implanted in two blood vessels in each pig. Pigs used in this model were generally 2-4 months old and weighed 30-40 Kg. Two coronary stents were thus implanted in each pig by visually assessing a "normal" stent:artery ratio of 1.1-1.2.

Beginning on the day of the procedure, pigs were given oral aspirin (325 mg daily) and continued for the remainder of their course. General anesthesia was achieved by means of intramuscular injection followed by intravenous ketamine (30 mg/kg) and xylazine (3 mg/kg). Additional medication at the time of induction included atropine (1 mg) and flocillin (1 g) administered intramuscularly. During the stenting procedure, an intra-arterial bolus of 10,000 units of heparin was administered.

Arterial access was obtained by cutdown on the right external carotid and placement of an 8F sheath. After the procedure, the animals were maintained on a normal diet without cholesterol or other special supplementation.

The BiodivYsio stent was used with nominal vessel target size of 3.0 mm. See FIG. 2. Two coronary arteries per pig were assigned at random to deployment of the stents. The stent was either a drug eluting stent (polymer plus drug stent) or a stent coated with a polymer only (polymer only stent). The stents were delivered by means of standard guide catheters and wires. The stent balloons were inflated to appropriate sizes for less than 30 seconds.

Each pig had one polymer only stent and one polymer plus drug stent placed in separate coronary arteries, so that each pig would have one stent for drug and one for control.

A sample size of 20 pigs total was chosen to detect a projected difference in neointimal thickness of 0.2 mm with a standard deviation of 0.15 mm, at a power of 0.95 and beta 0.02.

Animals were euthanized at 28 days for histopathologic examination and quantification. Following removal of the heart from the perfusion pump system, the left atrial appendage was removed for access to the proximal coronary arteries. Coronary arterial segments with injuries were dissected free of the epicardium. Segments containing lesions was isolated, thereby allowing sufficient tissue to contain uninvolved blood vessel at either end. The foregoing segments, each roughly 2.5 cm in length, were embedded and processed by means of standard plastic embedding techniques. The tissues were subsequently processed and stained with hematoxylin-eosin and elastic-van Gieson techniques.

Low and high power light microscopy were used to make length measurements in the plane of microscopic view by means of a calibrated reticle and a digital microscopy system connected to a computer employing calibrated analysis software.

The severity of vessel injury and the neointimal response were measured by calibrated digital microscopy. The importance of the integrity of the internal elastic lamina is well-known to those skilled in the art. A histopathologic injury score in stented blood vessels has been validated as being closely related to neointimal thickness. This score is related to depth of injury and is as follows:

| Score | Description of Injury |
|---|---|
| 0 | Internal elastic lamina intact; endothelium typically denuded, media compressed but not lacerated. |
| 1 | Internal elastic lamina lacerated; media typically compressed but not lacerated. |
| 2 | Internal elastic lacerated; media visibly lacerated; external elastic lamina intact but compressed. |
| 3 | External elastic lamina lacerated; typically large lacerations of media extending through the external elastic lamina; coil wires sometimes residing in adventitia. |

This quantitative measurement of injury was assessed for all stent wires of each stent section. The calibrated digital image was also used to measure at each stent wire site the neointimal thickness. Lumen area, area contained with the internal elastic lamina, and area within the external elastic lamina were also measured.

The neointimal thickness measured were for each strut in a given section than averaged to determine the neointimal thickness for the section.

The mid-stent segment was used for measurement, analysis, and comparison. Data were also recorded (and included in the data section of this report) for proximal and distal segments.

The data analysis methods for this study did not need to take into account variable arterial injury across treatment/control groups, because mild to moderate injury is sensitive enough to detect treatment differences. Paired t-testing was performed to compare variables across the polymer only stents (control group) and polymer plus drug stents (treatment group). No animal died in this study before scheduled timepoints.

Table 3 shows the pigs and arteries used. In Table 3, LCX means the circumflex branch of the left coronary artery, LAD means the left anterior descending coronary artery, and RCA means the right coronary artery.

TABLE 3

| | Pigs and Vessels Used | |
|---|---|---|
| 1 | 2000-G-693 | RCA - Control |
| | 2000-G-693 | LCX - Test |
| 2 | 2000-G-698 | RCA - Test |
| | 2000-G-698 | LAD - Control |
| 3 | 2000-G-702 | RCA - Test |
| | 2000-G-702 | LAD - Control |
| 4 | 2000-G-709 | RCA - Control |
| | 2000-G-709 | LAD - Test |
| 5 | 2000-G-306 | RCA - Control |
| | 2000-G-306 | LAD - Test |
| | 2000-G-306 | * LCX - Test |
| 6 | 2000-G-672 | RCA - Test |
| | 2000-G-672 | LAD - Control |

TABLE 3-continued

Pigs and Vessels Used

| | | |
|---|---|---|
| 7 | 2000-G-712 | RCA - Control |
| | 2000-G-712 | LCX - Test |
| 8 | 2000-G-735 | RCA - Control |
| | 2000-G-735 | LAD - Test |
| 9 | 2000-G-736 | RCA - Control |
| | 2000-G-736 | LCX - Test |
| 10 | 2000-G-740 | RCA - Test |
| | 2000-G-740 | LAD - Control |
| 11 | 2000-G-742 | LAD - Test |
| | 2000-G-742 | OM (LCX) - Control |
| 12 | 2000-G-744 | RCA - Test |
| | 2000-G-744 | LAD - Control |
| 13 | 2000-G-748 | RCA - Test |
| | 2000-G-748 | LAD - Control |
| 14 | 2000-G-749 | RCA - Control |
| | 2000-G-749 | LCX - Test |
| 15 | 2000-G-753 | RCA - Control |
| 16 | 2000-G-753 | LAD - Test |
| | 2000-G-754 | RCA - Test |
| | 2000-G-754 | LCX - Control |
| 17 | 2000-G-755 | RCA - Control |
| | 2000-G-755 | LAD - Test |
| 18 | 2000-G-756 | RCA - Test |
| | 2000-G-756 | LAD - Control |
| 19 | 2000-G-757 | LAD - Control |
| | 2000-G-757 | LCX - Test |
| 20 | 2000-G-760 | LAD - Test |
| | 2000-G-760 | LCX - Control |

Table 4 shows the summary results for all data for mean injury and neointimal thickness for each stent, including proximal, mid, and distal segments. Table 4 also shows lumen size, percent stenosis, and artery size as measured by the internal elastic laminae (IEL) and external elastic laminae (EEL).

TABLE 4

Summary: All Measures (Distal, Mid, Proximal)

| ID | | prox ref | dist ref | lumen | IEL | EEL | mean injury | % stenosis | Neointimal area | NIT |
|---|---|---|---|---|---|---|---|---|---|---|
| Control | Distal | | | | | | | | | |
| Mean | | 4.46 | 3.96 | 4.88 | 7.66 | 9.00 | 0.22 | 36.10 | 2.79 | 0.41 |
| SD | | 1.20 | 1.16 | 1.30 | 1.15 | 1.10 | 0.26 | 15.41 | 1.29 | 0.17 |
| Control | Mid | | | | | | | | | |
| Mean | | 4.46 | 3.96 | 4.94 | 7.71 | 9.08 | 0.08 | 36.23 | 2.77 | 0.38 |
| SD | | 1.20 | 1.16 | 1.44 | 1.07 | 1.15 | 0.14 | 14.93 | 1.20 | 0.16 |
| Control | Proximal | | | | | | | | | |
| Mean | | 4.46 | 3.96 | 5.11 | 7.89 | 9.30 | 0.15 | 35.35 | 2.78 | 0.38 |
| SD | | 1.20 | 1.16 | 1.38 | 1.33 | 1.42 | 0.22 | 11.94 | 1.04 | 0.12 |
| Test | Distal | | | | | | | | | |
| Mean | | 4.26 | 3.41 | 6.04 | 7.70 | 9.01 | 0.26 | 22.35 | 1.66 | 0.25 |
| SD | | 1.26 | 0.96 | 1.55 | 1.49 | 1.47 | 0.43 | 8.58 | 0.58 | 0.06 |
| Test | Mid | | | | | | | | | |
| Mean | | 4.26 | 3.41 | 6.35 | 7.75 | 8.98 | 0.04 | 18.71 | 1.41 | 0.22 |
| SD | | 1.26 | 0.96 | 1.29 | 1.18 | 1.31 | 0.07 | 5.68 | 0.33 | 0.05 |
| Test | Proximal | | | | | | | | | |
| Mean | | 2.56 | 2.15 | 3.31 | 4.06 | 4.66 | 0.19 | 16.79 | 1.29 | 0.18 |
| SD | | 1.66 | 1.37 | 2.39 | 3.48 | 4.15 | 0.13 | 9.97 | 0.80 | 0.12 |

There was no statistically significant difference for neointimal area or thickness across proximal, mid, or distal segments within the test group (polymer plus drug stents) or control groups (polymer only stents). This observation is quite consistent with prior studies, and thus allows use of only the mid segment for statistical comparison of test devices (polymer plus drug stents) vs. control devices (polymer only stents).

Table 5 shows the statistical t-test comparisons across test groups and control groups. There was a statistically significant difference in neointimal thickness, neointimal area, lumen size, and percent lumen stenosis, the drug eluting stent being clearly favored. Conversely, there were no statistically significant differences between the test group (polymer plus drug stents) and the control group (polymer only stents) for mean injury score, external elastic laminae, or internal elastic laminae areas.

TABLE 5

Statistical Comparison of Test vs. Control Parameters: Mid-Section Data
t-test Statistics

| Parameter | Difference | t-test | DF | Std Error | Lower 95% | Upper 95% | p |
|---|---|---|---|---|---|---|---|
| Lumen | −1.17 | −2.28 | 38 | 0.52 | −2.21 | −0.13 | 0.029 |
| IEL | 0.03 | 0.088 | 38 | 0.36 | −0.71 | 0.78 | 0.93 |

TABLE 5-continued

Statistical Comparison of Test vs. Control Parameters: Mid-Section Data
t-test Statistics

| Parameter | Difference | t-test | DF | Std Error | Lower 95% | Upper 95% | p |
|---|---|---|---|---|---|---|---|
| EEL | 0.2 | 0.499 | 38 | 0.39 | −0.599 | 0.99 | 0.62 |
| NI Thickness | 0.18 | 5.153 | 38 | 0.034 | 0.106 | 0.244 | <.0001 |
| NI Area | 1.21 | 3.62 | 38 | 0.33 | 0.53 | 1.88 | 0.0008 |
| Mean Injury | 0.038 | 1.137 | 38 | 0.033 | −0.02 | 0.106 | 0.26 |
| % Stenosis | 14.54 | 2.97 | 38 | 4.9 | 4.61 | 24.47 | 0.005 |

The reference arteries proximal and distal to the stented segments were observed, and quantitated. These vessels appeared normal in all cases, uninjured in both the control group (polymer only stents) and the test group (polymer plus drug stents). See FIGS. 3A and 3B. The data below show there were no statistically significant differences in size between the stents in the control group and the stents in the test group.

| | Proximal Reference Diameter (mm) | Distal Reference Diameter (mm) |
|---|---|---|
| Control (mean + SD) | 4.46 + 1.20 | 3.96 + 1.16 |
| Test (mean + SD) | 4.26 ± 1.26 | 3.41 + 0.96 |

The data suggest that statistically significant differences exist, and these differences favor the stent that elutes A-179578. The stent of this invention results in lower neointimal area, lower neointimal thickness, and greater lumen area. There were no significant differences within the test group (polymer plus drug stents) and the control group (polymer only stents) for neointimal or injury parameters. There were no significant differences in artery sizes (including the stent) for the control group compared to the test group. These latter findings suggest no significant difference in the arterial remodeling characteristics of the polymeric coating containing the drug.

At most, mild inflammation was found on both the polymer plus drug stent and the polymer only stent. This finding suggests that the polymer exhibits satisfactory biocompatibility, even without drug loading. Other studies show that when drug has completely gone from the polymer, the polymer itself creates enough inflammation to cause neointima. This phenomenon may be responsible for the late □catch-up□ phenomenon of clinical late restenosis. Because the polymer in this example did not cause inflammation in the coronary arteries, late problems related to the polymer after the drug is exhausted are unlikely.

In conclusion, a stent containing the compound A-179578 with a polymer showed a reduction in neointimal hyperplasia in the porcine model when placed in a coronary artery.

Example 4

The purpose of this example is to determine the rate of release of the A-179578 drug from 316L Electropolished Stainless Steel Coupons coated with a biocompatible polymer containing phosphorylcholine side groups.

Rubber septa from lids from HPLC vials were removed from the vials and placed into glass vials so that the "Teflon" side faced up. These septa served as supports for the test samples. The test samples were 316L stainless steel coupons that had been previously coated with a biocompatible polymer containing phosphorylcholine side groups (PC polymer). Coronary stents are commonly made of 316L stainless steel and can be coated with the PC polymer to provide a depot site for loading drugs. The coated coupons, which serve to simulate stents, were placed onto the septa. By using a glass Hamilton Syringe, a solution of A-179578 and ethanol (10 μl) was applied to the surface of each coupon. The solution contained A-179578 (30.6 mg) dissolved in 100% ethanol (3.0 ml). The syringe was cleaned with ethanol between each application. The cap to the glass vial was placed on the vial loosely, thereby assuring proper ventilation. The coupon was allowed to dry for a minimum of 1.5 hours. Twelve (12) coupons were loaded in this way—six being used to determine the average amount of drug loaded onto the device and six being used to measure the time needed to release the drug from the devices.

To determine the total amount of ABT-578 loaded onto a coupon, a coupon was removed from the vial and placed into 50/50 acetonitrile/0.01M phosphate buffer (pH 6.0, 5.0 ml). The coupon was placed onto a 5210 Branson sonicator for one hour. The coupon was then removed from the solution, and the solution was assayed by HPLC.

The time release studies were performed by immersing and removing the individual coupons from fresh aliquots (10.0 ml) of 0.01 M phosphate buffer at a pH of 6.0 at each of the following time intervals—5, 15, 30 and 60 minutes. For the remaining time points of 120, 180, 240, 300, 360 minutes, volumes of 5.0 ml of buffer were used. To facilitate mixing during the drug release phase, the samples were placed onto an Eberbach shaker set at low speed. All solution aliquots were assayed by HPLC after the testing of the last sample was completed.

The HPLC analysis was performed with a Hewlett Packard series 1100 instrument having the following settings:
Injection Volume=100 μl
Acquisition Time=40 minutes
Flow Rate=1.0 ml/min
Column Temperature=40° C.
Wavelength=278 nm
Mobile Phase=65% Acetonitrile/35% H2O
Column=YMC ODS-A S5 μm, 4.6×250 mm Part No. A12052546WT The results from the above experiment showed the following release data:

TABLE 6

| Time (min.) | Percent Release | Standard Deviation |
|---|---|---|
| 0.00 | 0.00 | 0.00 |
| 5.00 | 1.87 | 1.12 |
| 15.00 | 2.97 | 1.47 |
| 30.00 | 3.24 | 1.28 |
| 60.00 | 3.29 | 1.29 |
| 120.00 | 3.92 | 1.28 |
| 180.00 | 4.36 | 1.33 |

TABLE 6-continued

| Time (min.) | Percent Release | Standard Deviation |
|---|---|---|
| 240.00 | 4.37 | 1.35 |
| 300.00 | 6.34 | 2.07 |
| 360.00 | 7.88 | 1.01 |

Example 5

The purpose of this example was to determine the loading and release of ABT-578 from 15 mm BiodivYsio drug delivery stents.

To load the stents with drug, a solution of ABT 578 in ethanol at a concentration of 50 mg/ml was prepared and dispensed into twelve vials. Twelve individual polymer-coated stents were placed on fixtures designed to hold the stent in a vertical position and the stents were immersed vertically in the drug solution for five minutes. The stents and fixtures were removed from the vials and excess drug solution was blotted away by contacting the stents with an absorbant material. The stents were then allowed to dry in air for 30 minutes in an inverted vertical position.

The stents were removed from the fixtures, and each stent was placed into 50/50 acetonitrile/phosphate buffer (pH 5.1, 2.0 ml) and sonicated for one hour. The stents were removed from the solution and solutions were assayed for concentration of drug, which allowed calculation of the amount of drug originally on the stents. This method was independently shown to remove at least 95% of the drug from the stent coating. On average, the stents contained 60 micrograms of drug ±20 micrograms.

The drug-loaded stents were placed on the fixtures and placed into 0.01 M phosphate buffer (pH=6.0, 1.9 ml) in individual vials. These samples were placed onto an Eberbach shaker set at low speed to provide back-and-forth agitation. To avoid approaching drug saturation in the buffer, the stents were transferred periodically to fresh buffer vials at the following points: 15, 30, 45, 60, 120, 135, 150, 165, 180, 240, 390 minutes. The dissolution buffer vials were assayed by HPLC for the drug concentration at the end of the drug release period studied. The data, represented as % cumulative release of the drug as a function of time, is shown in tabular form below:

TABLE 7

| Time (min) | % Cumulative Release of Drug |
|---|---|
| 15 | 0.3 |
| 30 | 1.1 |
| 45 | 2.1 |
| 60 | 3.2 |
| 120 | 4.3 |
| 135 | 5.9 |
| 150 | 6.3 |
| 165 | 6.8 |
| 180 | 7.4 |
| 240 | 10.8 |
| 390 | 13.2 |

Example 6

The purpose of this example was to evaluate the safety and efficacy of different drug dosages on neointima formation. Drug was delivered from the BiodivYsio OC stent (15 mm) coated with ABT-578. In-stent neointima formation was measured at four time intervals—3 days, 1 month, and 3 months—in the coronary arteries of adult miniature swine. Forty (40) animals were studied at each time interval (10 animals per dose). Each animal received one drug-coated stent and one control stent. The control stent contained no drug. Table 8 shows the dosing scheme for swine efficacy study.

TABLE 8

| | Dose group 1 (µg) | Dose group 2 (µg) | Dose group 3 (µg) | Dose group 4 (µg) |
|---|---|---|---|---|
| ABT-578 per stent | 15 | 45 | 150 | 400 |
| ABT-578 per mm of | 1 | 3 | 10 | 27 |

Potential local tissue toxicity was assessed at all time intervals by examining histopathologic changes in the stented region, adjacent coronary segments, perivascular tissue, and subserved myocardium. The mortality, angiographic implant and restudy data, histomorphometry data, and stent site histopathology were studied.

Three-Day Group

Histopathology in combination with scanning electron microscopy provided information regarding the short-term response to the implanted stent. The responses were similar in the control group and all dose groups, and the responses involved compression of the tunica media without remarkable necrosis, an accumulation of thrombus and inflammatory cells mostly localized to the stent struts, and early evidence of endothelial recovery and smooth muscle cell invasion of the thin mural thrombi. There were no extensive thrombi or remarkable intramural hemorrhages. The adventitia in some samples displayed either focal or diffuse inflammatory infiltrates, and occasionally there was plugging or congestion of the vasa vasora. There was no evidence of medial necrosis in any sample.

Scanning electron microscopy showed similar appearance of the luminal surface three days after the implant of the coronary stent in all dose groups. The shape of the stent was clearly embedded in a thin layer of tissue. The endothelium was intact between the struts and even over the struts; a confluent or nearly confluent layer of endothelial-like cells had covered the luminal surface. There were scattered adherent platelets, platelet microthrombi, and leukocytes over the stents and on the intact remnant endothelium in the inter-strut spaces. In arteries with more severe stent-induced vessel damage, there were more substantial mural thrombi, but the extent of endothelial recovery over the stent struts did not appear retarded, regardless of the dosage of ABT-578.

One-Month Group

The histomorphometry data for the one-month series indicated a significant inhibitory effect of locally eluted ABT-578 on neointima formation in stented coronary arteries of swine. Intima area normalized to injury score was significantly decreased for dose groups 3 and 4 (10 and 27 µg/mm) as compared with the control; there were also trends for decreases in absolute intima area and intima thickness for both dose groups 3 and 4 as compared with the control, and a tendency towards decreased histologic % stenosis for dose group 3 as compared with the control.

The control stents displayed morphology typical of stents implanted in coronary arteries of Yucatan miniature swine at one month. The tunica media was compressed or thinned without necrosis subjacent to profiles of stent struts; there were only occasional inflammatory infiltrates; and the neointima ranged in size from relatively thin to moderately thin, and were composed of spindle-shaped and stellate cells in an abundant extracellular matrix, with only rare small foci of fibrinoid material around the profiles of the stent struts. The drug-coated stents showed similar compression of the tunica media without any substantial necrosis at any dose; like control devices, there was little inflammation present. The neointima was notably thinner in dose groups 3 and 4, in some cases being composed of only a few layers of cells. In all dose groups, there were substantial numbers of samples in which moderately sized fibrinoid deposits and inspissated thrombi were observed in the deep neointima. These were usually associated with the stent struts but sometimes extended between strut profiles. However, in no case was there exposure of thrombus on the luminal surface, as the deposits were encapsulated within fibrocellular tissue and covered with a flattened layer of periluminal endothelial-like cells.

Scanning electron microscopy confirmed that a confluent layer of endothelial or endothelial-like cells covered the entire stented surface, and there was no difference between drug-coated stents and control stents in terms of adherence of blood elements; leukocytes were present in approximately equal numbers in all groups. These findings demonstrate that while ABT-578 was associated with decreased neointima formation and persistent mural thrombi, sufficient vessel wall healing in response to stent injury had occurred within one month after the stent had been implanted. This vessel wall healing had rendered the luminal surface non-reactive for platelet adhesion and thrombus formation, and minimally reactive for leukocyte adherence. Additionally, there was no evidence of vessel wall toxicity even at the highest dose (27 μg/mm), as there was no medial necrosis or stent malapposition.

Three-Month Group

There were no significant differences between the dose groups for any histomorphometric parameters of stented coronary arterial dimension in the three-month period of the study. However, there were weak trends for decreases in the two primary variables describing neointima formation—the cross-sectional area and the % area stenosis of the lumen.

The histopathologic appearance of the control stents in the swine coronary artery samples at three months after the implant appeared similar to that of the controls from the one-month group, and similar to those of all the groups in the three-month period. All samples showed fibrocellular neointima formation with mostly spindle-shaped smooth muscle-like cells in the neointima and a confluent squamous periluminal cell layer. There were no intramural hemorrhages or persistent fibrinoid deposits in the neointima; however some samples, particularly those with thicker neointima, showed evidence of prior thrombus accumulation and subsequent organization in the form of neovascularization in the neointima. On occasion, samples showed evidence of moderate to severe inflammatory reactions localized to the stent struts, associated with destruction of the tunica media architecture. These were most often associated with thicker neointima as well. However, these were few in number and were found in the control group as well as in the drug-coated stent groups. It is presumed that these represented either animal-specific generalized reactions to the implanted stent, evidence of contamination of the stent, or some combination of these two factors, and is commonly found at an incidence of about 10-15% in the studies of stent implants in swine coronary arteries. There was no evidence of necrosis of the tunica media or separation of the media from the stent in any sample. The adventitia of most three-month implants appeared to have somewhat greater neovascularization than did the one-month implants, but this did not appear related to control or test stent group. Scanning electron microscopy demonstrated confluent endothelium with rare adherent blood cells in the control group and all dose groups.

CONCLUSIONS

The stent coated with ABT-578 reduced in-stent neointima formation in swine coronary arteries and provided clear evidence of a biologic drug effect (unresorbed thrombus/fibrin deposits of neointima) at one month. There was a weak tendency for the stent coated with ABT-578 to show a persistent inhibitory effect at the longer-term time interval of three months. There was no local coronary arterial wall toxicity in the form of medial necrosis or stent malapposition associated with any dose group, including the highest dose of approximately 27 μg/mm stent length at any time interval examined. All stents were well incorporated into the tissue, and there was evidence of stable healing responses in the form of fibrocellular neointimal incorporation and endothelial coverage at the one-month interval and at the three-month interval. The trend towards a sustained inhibitory effect at three months after the stent was implanted in this animal is surprising and provides evidence for potentially persistent effects in preventing clinical restenosis resulting from implanted stents.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A compound of formula:

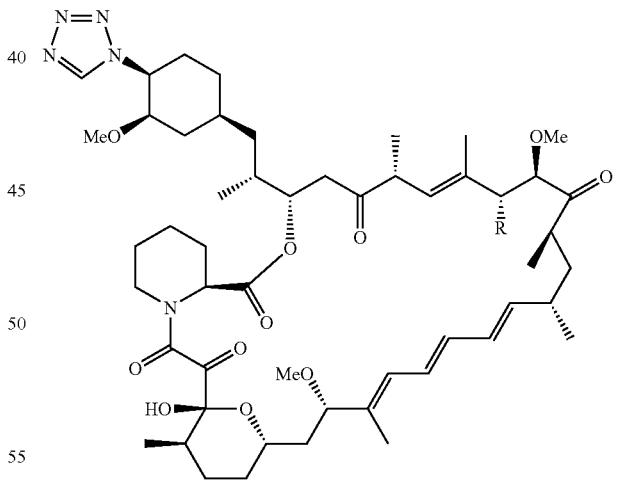

wherein R is $R^1C(O)R^2R^3$ or $R^1C(S)R^2R^3$ and wherein,
$R^1$ is O or S;
$R^2$ is a valence bond, O, NH or S; and
$R^3$ is alkyl, alkenyl, alkynyl, or aryl.

2. A method for inhibiting or treating restenosis, intimal smooth muscle cell hyperplasia, and vascular occulation in a mammal in need of treatment using the compound of claim 1.

3. A method for treating post-transplant-tissue transplant rejection in a mammal in need of treatment using the compound of claim 1.

4. A method for inhibiting or treating fungal growth in a mammal in need of treatment using the compound of claim 1.

5. The compound of claim 1, wherein R is $OC(O)R^2R^3$, wherein $R^2$ is a valence bond and $R^3$ is alkyl, alkenyl, alkenyl, or aryl.

6. A pharmaceutical composition comprising the compound of claim 1 and a pharmaceutically acceptable carrier or excipient.

* * * * *